US010739356B2

(12) United States Patent
Esnault et al.

(10) Patent No.: US 10,739,356 B2
(45) Date of Patent: Aug. 11, 2020

(54) PROGNOSIS AND MONITORING OF MEMBRANOUS NEPHROPATHY BASED ON THE ANALYSIS OF PLA2R1 EPITOPE PROFILE AND SPREADING

(71) Applicants: CHU DE NICE, Nice (FR); CENTRE NATIONAL DE LA RECHERCHE SCIENTIFIQUE—CNRS, Paris (FR); UNIVERSITÉ DE NICE SOPHIA ANTIPOLIS, Nice (FR)

(72) Inventors: Vincent Louis Marie Esnault, Nice (FR); Barbara Polski, La Trinité (FR); Gérard Jean Frantz Lambeau, Cabris (FR); Guillaume Dolla, Valbonne (FR)

(73) Assignees: Université de Nice Sophia Antipolis, Nice (FR); Centre National de la Recherche Scientifique (CNRS), Paris (FR); CHU de Nice, Nice (FR)

(*) Notice: Subject to any disclaimer, the term of this patent is extended or adjusted under 35 U.S.C. 154(b) by 68 days.

(21) Appl. No.: 15/742,484

(22) PCT Filed: Jul. 8, 2016

(86) PCT No.: PCT/EP2016/066320
§ 371 (c)(1),
(2) Date: Jan. 5, 2018

(87) PCT Pub. No.: WO2017/009245
PCT Pub. Date: Jan. 19, 2017

(65) Prior Publication Data
US 2018/0203020 A1    Jul. 19, 2018

(30) Foreign Application Priority Data

Jul. 10, 2015    (EP) .................................... 15306148

(51) Int. Cl.
G01N 33/53    (2006.01)
G01N 33/68    (2006.01)

(52) U.S. Cl.
CPC ..... *G01N 33/6893* (2013.01); *G01N 33/6878* (2013.01); *G01N 2333/705* (2013.01); *G01N 2800/347* (2013.01); *G01N 2800/52* (2013.01)

(58) Field of Classification Search
None
See application file for complete search history.

(56) References Cited

FOREIGN PATENT DOCUMENTS

| WO | 2010/009457 A1 | 1/2010 |
| WO | 2015/004603 A1 | 1/2015 |
| WO | 2015/185949 A1 | 12/2015 |

OTHER PUBLICATIONS

Van Der Vekiens et al., Human and equine cardiovascular endocrinology: beware to compare, Cardiovascular Endocrinology 2013, vol. 2, No. 4, pp. 67-76 (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Akiyama et al., "Prevalence of anti-phospholipase A2 receptor antibodies in Japanese patients with membranous nephropathy," *Clin Exp Nephrol* 19(4):653-660, 2015 (8 pages).
Bech et al., "Association of Anti-PLA2R Antibodies with Outcomes after Immunosuppressive Therapy in Idiopathic Membranous Nephropathy," *Clinical Journal of the American Society of Nephrology* 9, 2014, 9 pages.
Beck et al., "M-Type Phospholipase $A_2$ Receptor as Target Antigen in Idiopathic Membranous Nephropathy," *The New England Journal of Medicine* 361(1):11-21, 2009.
Beck et al., "Rituximab-Induced Depletion of Anti-$PLA_2R$ Autoantibodies Predicts Response in Membranous Nephropathy," *J Am Soc Nephrol* 22:1543-1550, 2011.
Behnert et al., "An Anti-Phospholipase $A_2$ Receptor Quantitative Immunoassay and Epitope Analysis in Membranous Nephropathy Reveals Different Antigenic Domains of the Receptor," *PLoS ONE* 8(4):e61669, 2013 (9 pages).
Coenen et al., "Phospholipase A2 Receptor (PLA2R1) Sequence Variants in Idiopathic Membranous Nephropathy," *J Am Soc Nephrol* 24, 2013, 10 pages.
Dähnrich et al., "Development of a standardized ELISA for the determination of autoantibodies against human M-type phospholipase A2 receptor in primary membranous nephropathy," *Clinica Chimica Acta* 421:213-218, 2013.
Dai et al., "Diagnostic accuracy of PLA2R autoantibodies and glomerular staining for the differentiation of idiopathic and secondary membranous nephropathy: an updated meta-analysis," *Scientific Reports* 5:8803, 2015 (9 pages).
Du et al., "The Diagnosis Accuracy of PLA2R-AB in the Diagnosis of Idiopathic Membranous Nephropathy: A Meta-Analysis," *PLoS ONE* 9(8):e104936, 2014 (7 pages).
Francis et al., "Membranous Nephropathy: A Journey From Bench to Bedside," *Am J Kidney Dis.* 68(1):138-147, 2016.
Fresquet et al., "Identification of a Major Epitope Recognized by PLA2R Autoantibodies in Primary Membranous Nephropathy," *J Am Soc Nephrol* 26:302-313, 2015.
Glassock, "Antiphospholipase A2 Receptor Autoantibody Guided Diagnosis and Treatment of Membranous Nephropathy: A New Personalized Medical Approach," *Clin J Am Soc Nephrol* 9:1341-1343, 2014.
Hofstra et al., "Antiphospholipase $A_2$ Receptor Antibody Titer and Subclass in Idiopathic Membranous Nephropathy," *J Am Soc Nephrol* 23, 2012, 13 pages.

(Continued)

Primary Examiner — Gary Counts
(74) Attorney, Agent, or Firm — W&C IP

(57) ABSTRACT

Disclosed is a method for assessing the prognosis of idiopathic membranous nephropathy in a body fluid sample from a human subject, based on profiling PLA2R1 epitopes recognized by autoantibodies in the sample. The method further relates to analysis of PLA2R1 epitope spreading amongst three PLA2R1 domains (Cys R, CTLD1 and CTLD7) that are recognized by anti-PLA2R1 autoantibodies, two of which (CTLD1 and CTLD7) are more closely associated with active idiopathic membranous nephropathy and likely linked by a mechanism of epitope spreading.

7 Claims, No Drawings

(56) References Cited

OTHER PUBLICATIONS

Hoxha et al., "Phospholipase A2 Receptor Autoantibodies and Clinical Outcome in Patients with Primary Membranous Nephropathy," *J Am Soc Nephrol* 25:1357-1366, 2014.

Hu et al., "Diagnostic value of phospholipase A2 receptor in idiopathic membranous nephropathy: a systematic review and meta-analysis," *J Nephrol* 27(2):111-116, 2014 (abstract only, 3 pages).

Kanigicherla et al., "Anti-PLA2R antibodies measured by ELISA predict long-term outcome in a prevalent population of patients with idiopathic membranous nephropathy," *Kidney International* 83:940-948, 2013.

Kao et al., "Identification of the Immunodominant Epitope Region in Phospholipase $A_2$ Receptor-Mediating Autoantibody Binding in Idiopathic Membranous Nephropathy," *J Am Soc Nephrol* 26:291-301, 2015.

Ronco et al., "Pathophysiological advances in membranous nephropathy: time for a shift in patient's care," *Lancet* 385:1983-1992, 2015.

Ruggenenti et al., "Anti-Phospholipase $A_2$ Receptor Antibody Titer Predicts Post-Rituximab Outcome of Membranous Nephropathy," *J Am Soc Nephrol* 26:2545-2558, 2015.

Seitz-Polski et al., "Cross-reactivity of anti-PLA2R1 autoantibodies to rabbit and mouse PLA2R1 antigens and development of two novel ELISAs with different diagnostic performances in idiopathic membranous nephropathy," *Biochimie* 118:104-115, 2015.

Seitz-Polski et al., "Epitope Spreading of Autoantibody Response to PLA2R Associates with Poor Prognosis in Membranous Nephropathy," *J Am Soc Nephrol* 27:1517-1533, 2016.

Seitz-Polski et al., "Prediction of membranous nephropathy recurrence after transplantation by monitoring of anti-PLA2R1 (M-type phospholipase A2 receptor) autoantibodies: a case series of 15 patients," *Nephrol Dial Transplant* 29:2334-2342, 2014.

Stanescu et al., "Risk HLA-DQA1 and $PLA_2R1$ Alleles in Idiopathic Membranous Nephropathy," *N Engl J Med* 364(7):616-626, 2011.

Timmermans et al., "Anti-PLA2R Antibodies as a Prognostic Factor in PLA2R-Related Membranous Nephropathy," *Am J Nephrol* 42:70-77, 2015.

\* cited by examiner

PROGNOSIS AND MONITORING OF MEMBRANOUS NEPHROPATHY BASED ON THE ANALYSIS OF PLA2R1 EPITOPE PROFILE AND SPREADING

FIELD OF THE INVENTION

The invention relates to a method for assessing the prognosis of membranous nephropathy in a subject, based on the analysis of PLA2R1 epitope profile. The invention further relates to a method for monitoring the progression of membranous nephropathy based on the analysis of the PLA2R1 epitope spreading.

BACKGROUND OF THE INVENTION

Idiopathic Membranous Nephropathy (iMN) is an autoimmune disease and a common cause of nephrotic syndrome in adults. Disease evolution is highly variable with spontaneous remission, persistent proteinuria or end-stage kidney disease. In 2009, Beck et al. identified the M-type phospholipase A2 receptor (PLA2R1) as the major podocyte antigen in iMN. The presence of anti-PLA2R1 autoantibodies has been widely confirmed in subsequent studies in 53 to 80% of iMN patients. The pathogenic role of these autoantibodies is not yet proven, but anti-PLA2R1 antibody titers appear to correlate with disease activity in most study populations.

However, individual outcome prediction from anti-PLA2R1 titers is unclear. Indeed, while autoantibodies disappear in most patients during remission, either under symptomatic or immunosuppressive treatments, it may persist during apparent clinical remission under renin-angiotensin system (RAS) blockade. Furthermore, high anti-PLA2R1 antibody titers appear to correlate with subsequent poor renal outcome in most cases but some patients with high autoantibody titers at onset exhibit a sharp decrease of anti-PLA2R1 activity and disease remission.

The treatment of iMN is controversial. KDIGO guidelines (Kidney Disease Improving Global Outcomes) recommend a supportive symptomatic treatment with blockers of the renin angiotensin system and diuretics in all patients with iMN, and immunosuppressive therapy only in case of renal function deterioration or persistent nephrotic syndrome.

Therefore, immunosuppressive treatments are often started only after significant and potentially irreversible complications. On the other hand, an unnecessarily early start of immunosuppression can be futile in patients who might develop remission with symptomatic treatments. Therefore, there is a need for better predictors of the outcome of patients suffering from idiopathic Membranous Nephropathy.

There is thus a long-time felt need for the development of comprehensive, sensitive, and specific methods for the prognosis of idiopathic Membranous Nephropathy. In addition, there is an unfulfilled need for a method for stratifying patients for responsiveness to their treatments in order to provide necessary modifications to ineffective therapeutic regimens.

SUMMARY OF THE INVENTION

The M-type phospholipase A2 receptor (PLA2R1) is a 180 kDa membrane receptor with a large extracellular region comprising 10 distinct globular domains of 7 to 17 kDa, namely a cysteine-rich domain (CysR), a fibronectin type II domain (FNII) and eight distinct C-type lectin domains (CTLD1 to 8). Each domain is separated by a small linker sequence of about 10 amino acids.

The inventors first screened a cohort of 50 iMN patients for their reactivity against nine PLA2R1 mutants, successively deleting each of the 10 extracellular domains of the receptor. The inventors identified epitopes in three distinct domains:

Cysteine-rich domain (CysR) of PLA2R1;
C-type lectin domain 1 (CTLD1) of PLA2R1; and
C-type lectin domain 7 (CTLD7) of PLA2R1.

They then confirmed the independent reactivity of each domain by using numerous soluble forms of these domains by both western blot and ELISA. The inventors then set-up epitope-specific ELISAs and stratified a cohort of 69 patients into three epitope-specific subgroups and analyzed the relationships between their epitope profiles and disease activity. The inventors have thus shown that anti-PLA2R1 reactivity against CysR at serum sampling was associated with favorable outcome while reactivity against CTLD1 and CTLD7 was associated with active disease and poor renal prognosis.

Furthermore, they showed that the epitope profiles could change during follow-up. Anti-CTLD1 and anti-CTLD7 antibodies disappeared with disease remission and reappeared with disease relapse while anti-CysR restricted activity was associated with stable and mild disease activity.

Thus, in a first aspect, the invention relates to a method for assessing the prognosis of membranous nephropathy, preferably idiopathic membranous nephropathy, in a subject, said method comprising the step a) of detecting and/or measuring the level, in a biological sample obtained from said subject, of autoantibodies directed against the C-type lectin domain 1 (CTLD1) of PLA2R1; wherein the presence of autoantibodies directed against CTLD1 is indicative of a bad prognosis.

In a second aspect, the invention relates to a method for assessing the prognosis of membranous nephropathy, preferably idiopathic membranous nephropathy, in a subject, said method comprising the steps of:

contacting a biological sample obtained from said patient with a mouse PLA2R1, and detecting any antigen-antibody complex formed;
wherein the presence of any antigen-antibody complex formed is indicative of a bad prognosis.

In a third aspect, the invention relates to a method for monitoring the effectiveness of a treatment of membranous nephropathy, preferably idiopathic membranous nephropathy, in a subject, comprising:

determining at a first time point a level of at least one, preferably two, more preferably three autoantibodies selected from the group consisting of autoantibodies respectively directed against CysR, CTLD1 and CTLD7 in a biological sample obtained from said subject at said first time point, determining at a second time point a level of at least one, preferably two, more preferably three autoantibodies selected from the group consisting of autoantibodies respectively directed against CysR, CTLD1 and CTLD7 in a biological sample obtained from said subject at said second time point, and comparing the levels of autoantibodies of the two time points,
wherein:
the absence of autoantibodies respectively directed against CTLD1 and CTLD7 or the decrease of the levels of autoantibodies respectively directed against CTLD1 and CTLD7 in the second time point indicates that the treatment is effective; and/or the presence of autoantibodies directed against CTLD1 and/or CTLD7 or the increase in the levels of autoantibodies directed against CTLD1 and/or CTLD7 at the second time point indicates that the treatment is not effective.

In a fourth aspect, the invention relates to a method for diagnosing membranous nephropathy particularly idiopathic membranous nephropathy, in a subject, said method comprising the step a') of detecting in a biological sample obtained from said subject, at least one autoantibody selected from the group consisting:

autoantibodies directed against the Cysteine-rich domain (CysR) of PLA2R1; and/or autoantibodies directed against the C-type lectin domain 1 (CTLD1) of PLA2R1; and/or autoantibodies directed against the C-type lectin domain 7 (CTLD7) of PLA2R1, wherein, the presence of one, preferably two and more preferably three from autoantibodies directed against CysR, CTLD1, and/or CTLD7 of PLA2R1 is indicative of membranous nephropathy, preferably idiopathic membranous nephropathy.

DETAILED DESCRIPTION OF THE INVENTION

Method for Prognosing Idiopathic Membranous Nephropathy

The M-type phospholipase A2 receptor (PLA2R1) is the major autoantigen in idiopathic membranous nephropathy, with two recently identified epitopes of unknown clinical significance. Here, fifty PLA2R1-positive patients' sera were screened by western blot on a series of PLA2R1 deletion mutants covering the ten extracellular domains. The inventors identified epitopes in the CysR, CTLD1 and CTLD7 domains and confirmed the reactivity against these three domains with soluble forms of each domain. Domain-specific ELISAs allowed stratifying 69 PLA2R1-positive patients into three subgroups: 23 CysR, 14 CysR+CTLD1 and 32 CysR+CTLD1+CTLD7. Median ELISA titers measured using the full-length PLA2R1 antigen were not statistically different between patients' subgroups. The 23 patients with anti-CysR restricted activity were younger ($p=0.008$), had less nephrotic range proteinuria ($p=0.018$) and exhibited more spontaneous remission ($p=0.03$), lower rate of renal failure progression ($p=0.0025$) and less end-stage kidney disease ($p=0.01$) during follow-up. Indeed, 31/69 patients had poor renal prognosis according to KDIGO (urinary protein/creatinine ratio over 4 g/g or eGFR<45 ml/min/1.73 m$^2$ at end of follow-up). High anti-PLA2R1 activity and epitope spreading beyond CysR epitope were independent risk factors of poor renal prognosis in multivariable cox regression analysis. Epitope spreading during follow-up was associated with disease worsening (n=3), whereas reverse spreading from CTLD7 profile back to CysR was associated with favorable outcome (n=1).

The inventors have met the burden to show that anti-PLA2R1 reactivity against CysR at serum sampling was associated with favorable outcome while reactivity against CTLD1 and CTLD7 was associated with active disease and poor renal prognosis. Further, the inventors have highlighted that the reactivity against CTLD1 is relevant enough for assessing the prognosis of idiopathic membranous nephropathy.

Therefore, in a first aspect, the invention relates to a method for assessing the prognosis of membranous nephropathy, preferably idiopathic membranous nephropathy, in a subject, said method comprising the step a) of detecting and/or measuring the level, in a biological sample obtained from said subject, of autoantibodies directed against the C-type lectin domain 1 (CTLD1) of PLA2R1; wherein the presence of autoantibodies directed against CTLD1 is indicative of a bad prognosis.

The inventors have shown that the detection of autoantibodies directed against C-type lectin domain 7 (CTLD7) in addition to autoantibodies directed against CTLD1 is associated with a worsening of the disease. Thus, in a further embodiment, said step a) further comprises detecting and/or measuring the level of autoantibodies directed against C-type lectin domain 7 (CTLD7) of PLA2R1. In this embodiment, the presence of autoantibodies directed against CTLD1 and/or autoantibodies directed against CTLD7 is indicative of a bad prognosis.

In a preferred embodiment, said step a) further comprises detecting and/or measuring the level of autoantibodies directed against the Cysteine-rich domain (CysR) of PLA2R1.

In yet a preferred embodiment, the invention relates to a method for assessing the prognosis of membranous nephropathy, preferably idiopathic membranous nephropathy, in a subject, said method comprising the step a) of detecting and/or measuring the level, in a biological sample obtained from said subject, of:

autoantibodies directed against the Cysteine-rich domain (CysR) of PLA2R1; and autoantibodies directed against the C-type lectin domain 1 (CTLD1) of PLA2R1; and autoantibodies directed against C-type lectin domain 7 (CTLD7) of PLA2R1;

wherein:

the presence of autoantibodies directed against CTLD1 and/or autoantibodies directed against CTLD7 is indicative of a bad prognosis.

Preferably, the method of the invention is further characterized in that:

the absence of autoantibodies respectively directed against CysR, CTLD1, CTLD7 is indicative of a good prognosis; and/or the presence of autoantibodies directed only against CysR is indicative of a good prognosis.

Typically, the presence of autoantibodies directed against CysR and autoantibodies directed against CTLD1 and/or CTLD7 is indicative of a bad prognosis.

The term "membranous nephropathy" has its general meaning in the art and refers to a renal disease which is a frequent cause of adult nephrotic syndrome. It encompasses secondary membranous nephropathies that are caused by secondary factors such as systemic lupus erythematosus, hepatitis B, or syphilis ( . . . ), and primary autoimmune membranous nephropathy, also called "idiopathic membranous nephropathy. "Idiopathic membranous nephropathy" is considered to be an autoimmune disease targeting the kidney glomerulus, the major known target autoantigen being PLA2R1.

The term "PLA2R1" or "secretory phospholipase A2 receptor" refers to the M-type phospholipase A2 receptor, a receptor encoded in humans by the PLA2R1 gene, particularly known as a major autoantigen in idiopathic membranous nephropathy. An exemplary human native PLA2R1 amino acid sequence is provided in NP_001007268 (GenPept database).

The term "autoantibody" has its general meaning in the art and refers to an antibody that is produced by the immune system of a subject and that is directed against subject's own proteins (for example specific domains of PLA2R1). Autoantibodies may attack the body's own cells, tissues, and/or organs, causing inflammation and cell injury.

As used herein, the expressions "autoantibodies directed against CysR, CTLD1 and CTLD7", and "autoantibodies of the invention" refer to autoantibodies that respectively recognize the Cysteine-rich domain (CysR) of PLA2R1; the C-type lectin domain 1 (CTLD1) of PLA2R1; and the C-type lectin domain 7 (CTLD7) of PLA2R1.

As used herein, the term "subject" or "patient" refers to an individual with symptoms of and/or suspected of suffering from idiopathic membranous nephropathy. In the context of the invention, the subject or patient is preferably a subject suffering or suspected of suffering from idiopathic membranous nephropathy.

The method of the invention provides crucial information to the practitioner in order for him to determine the appropriate therapeutic strategy to deploy and/or decide whether the patient may benefit from therapy. Typically, the method allows the identification of patient that might require hemodialysis or are at risk of kidney failure.

The expression "prognosis" as used herein refers to predicting the course or outcome of an idiopathic membranous nephropathy condition in a subject. This does not refer to the ability to predict the course or outcome of a condition with 100% accuracy, or even that a given course or outcome is predictably more or less likely to occur based on the pattern of biomarkers. Instead, the person skilled in the art will understand that the expression "prognosis" refers to an increased probability that a certain course or outcome will occur.

Preferably, in the context of the present invention, "good prognosis" refers to a high chance of remission and/or preferably a low risk of requiring hemodialysis and/or a low risk of developing kidney failure.

Subjects considered as having a good prognosis according to the method of the invention would thus not be in need of hemodialysis. Further, said subjects would not need to be subjected to an aggressive immunosuppressive treatment. Indeed, the method of the invention allows the identification of patients shaving a high chance of spontaneous remission. Typically, "spontaneous remission" is defined by remission induced by symptomatic treatment (such as RAS blockers and diuretics) without immunosuppressive treatment.

Preferably, in the context of the present invention, "bad prognosis" refers to a high chance of onset of subsequent renal complication, such a kidney failure and/or a high chance of relapse.

Bad prognosis is typically associated with:

an increased proteinuria, typically a proteinuria>4 g/g; and/or a serum creatinine increased over 30%; and/or an estimated glomerular filtration rate (eGFR)<45 ml/min/1.73 m$^2$.

The eGFR is used to screen for and detect early kidney damage and to monitor kidney status. It is performed by doing a creatinine test and calculating the estimated glomerular filtration rate.

Typically, subjects considered as having a bad prognosis according to the method of the invention would be in need of hemodialysis. Further, said subjects would need to be subjected to an immunosuppressive treatment. Indeed, the method of the invention allows the identification of patients shaving a low chance of spontaneous remission.

The method of the invention comprises a step of detecting and/or measuring the level of autoantibodies of the invention in a biological sample. Preferably, said biological sample is obtained from said subject. Such samples include, but are not limited to, bodily fluids which may or may not contain cells, e.g., blood (e.g., whole blood, serum or plasma). Such samples also include biopsies (for example kidney biopsy). Preferably, said sample is a body fluid of said subject. Non-limiting examples of samples include, but are not limited to, whole blood sample, plasma or serum. Preferably, said biological sample is serum. The term biological sample also encompasses any material derived by processing a biological sample. Derived materials include, but are not limited to, cells (or their progeny) isolated from the sample or proteins extracted from the sample. Processing of a biological sample may involve one or more of: filtration, distillation, extraction, concentration, inactivation of interfering components, addition of reagents, and the like.

Step a) may be a step of quantitative, semi-quantitative or qualitative measure of autoantibodies of the invention. Preferably, said step a) is a step of measuring the level, in a biological sample obtained from said subject, of autoantibodies directed CysR of PLA2R1, autoantibodies directed against CTLD1 of PLA2R1; and autoantibodies directed against CTLD7 of PLA2R1.

In one embodiment, said step a) comprises the following substeps:

contacting a biological sample obtained from said patient with a PLA2R1, and detecting any antigen-antibody complex formed, wherein the presence of an antigen-antibody complex is indicative of membranous nephropathy, preferably Idiopathic Membranous Nephropathy.

Preferably, the PLA2R1 is selected from the group consisting of human PLA2R, rabbit PLA2R1, mouse PLA2R1 or their fragments thereof.

As used herein, "fragment" of PLA2R1 refers to a continuous element of PLA2R1. Typically, said fragment is a biologically active fragment, i.e it comprises one or more functional properties of PLA2R1.

In the context of the present invention, a "fragment" of PLA2R1 comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire amino acid sequence of PLA2R1.

Preferably, said fragment comprises at least 100, at least 200, at least 300, at least 400, at least 500, at least 600, at least 700, at least 800, at least 900, at least 1000, at least 1100, at least 1120, at least 1250, at least 1300, at least 1310, at least 1320 amino acids of the entire amino acid sequence of PLA2R1.

Preferably, said fragment is recognized by an autoantibody directed against PLA2R1. Preferably, said fragment is recognized an autoantibody directed against CysR, CTLD1 or CTLD7 of PLA2R1. Determining the ability of the fragment to interact with said autoantibodies can be accomplished by one of the methods described above or known in the art for determining direct binding.

Methods for measuring the levels of autoantibodies in a biological sample may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation. The reactions generally include revealing labels such as fluorescent, chemiluminescent, radioactive, enzymatic labels or dye molecules, or other methods for detecting the formation of a complex between the antigen and the antibody or antibodies reacted therewith.

In a preferred embodiment, step a) is performed by ELISA. The term "ELISA" as used herein means an enzyme linked immunosorbent assay, a type of competitive binding assay comprising antibodies and a detectable label used to quantitate the amount of an analyte in a sample.

Said step a) of the invention thus allows evaluating the titers for autoantibodies directed against CysR, CTLD1 and CTLD7. Typically, in the context of the ELISA, the wells of a microtiter plate are coated with a set of target antigens. The biological samples are added to the coated wells. After a period of incubation sufficient to allow the formation of autoantibody-antigen complexes, the plate(s) can be washed to remove unbound moieties and a detectably labelled secondary binding antibody is added. The secondary binding molecule is allowed to react with any captured human autoantibody, the plate washed and the presence of the secondary binding antibody is detected using methods well known in the art.

It is noteworthy to note that human anti-PLA2R1 autoantibodies are selected among the following isotypes: IgG1, IgG2, IgG3 and IgG4. Preferably, human anti-PLA2R1 autoantibodies is an IgG4. Basically, the antigens used for carrying out the ELISA in the context of the invention are:
the CysR domain produced in HEK293 cells or *E. coli*;
the CTLD1 domain produced in in HEK293 cells or *E. coli*; and
the CTLD6-7 or CTLD6 construct produced in HEK293 cells or *E. coli*.

The two antigenic domains produced in HEK cells may be HA-affinity captured on ELISA plates pre-coated with anti-HA antibody while the CTLD1 domain from *E. coli* can be directly coated or captured with anti-HA. Adsorbed antigens are then incubated with patients' sera followed by detection with a secondary anti-human IgG specific antibody which can be preferably anti-IgG4 antibody coupled to peroxidase, but also other secondary anti-IgG such as anti-total, anti-IgG1, -IgG2 and -IgG3 secondary antibodies.

Alternatively, all the previously disclosed antigens may be used in the context of the assay.

In a preferred embodiment, the anti-PLA2R1 autoantibodies are IgG4. Indeed, the inventors showed that the majority of anti-PLA2R1 autoantibodies found in patients are of the IgG4 subclass. However, subclasses of anti-PLA2R1 IgG1, IgG2, and IgG3 are also found. Thus, in the context of the invention, the subclasses of anti-PLA2R1 autoantibodies directed against CysR, CTLD1 and CTLD7 domains are preferably but not exclusively IgG4 autoantibodies.

The presence or the absence of autoantibodies can be determined by comparing the detected level or titer for each of the groups of autoantibodies to a reference level.

It is noteworthy that the presence of an autoantibody may be seen as a higher level in comparison with a reference level. Similarly, an absence of autoantibody may be seen as a lower level in comparison with a reference level.

In the context of the present invention, the term "control", when used to characterize a subject, refers to a subject that is healthy or to a patient that has been diagnosed with a specific disease other than renal disease or a renal disease other than idiopathic membranous nephropathy.

The term "control sample" refers to one, or more than one sample, that has been obtained from a healthy subject or from a patient diagnosed with a disease other than renal disorder.

The terms "normal" and "healthy" are used herein interchangeably. They refer to a subject that has not shown any symptom associated with renal disorder, and that has not been diagnosed with membranous nephropathy or other nephropathy. Preferably, a normal subject is not on medication affecting renal system and has not been diagnosed with any other disease. In certain embodiments, normal subjects have similar sex, age, and/or body mass index as compared with the subject from which the biological sample to be tested was obtained. The term "normal" is also used herein to qualify a sample obtained from a healthy subject.

As used herein, the term "reference level" refers to a level measured in a biological sample obtained from a control or preferably to an average of several levels measured in biological samples obtained from several controls. Typically, the skilled person in the art may determine said reference level in a biological sample, preferably serum, of at least 100 individuals known to be healthy. The mean value of the obtained ratios is then determined, according to well-known statistical analysis, so as to obtain the mean level of autoantibodies directed against CysR, CTLD1 and CTLD7. Said values are then considered as being normal and thus constitute a threshold value. In a specific and preferred embodiment, the PLA2R1 antigen used for prognosis is a mouse PLA2R1 or fragments thereof.

In this latter very specific embodiment, wherein step a) comprises the following substeps: contacting a biological sample obtained from said patient with a mouse PLA2R1, and detecting any antigen-antibody complex formed, wherein the presence of any antigen-antibody complex formed is indicative of a bad prognosis.

Indeed, the inventors' further experiments put in light that mouse PLA2R1 can be used for assessing the prognosis of iMN.

Therefore, in a second aspect, the invention relates to a method for assessing the prognosis of membranous nephropathy, preferably idiopathic membranous nephropathy, in a subject, said method comprising the steps of contacting a biological sample obtained from said patient with a mouse PLA2R1, and detecting any antigen-antibody complex formed; wherein the presence of any antigen-antibody complex formed is indicative of a bad prognosis.

Thus, in this aspect, the invention relies on the identification of autoantibodies directed against mouse PLA2R1. The invention thus aims to identify patients showing a bad prognosis.

Method for Monitoring the Effectiveness of the Response to a Treatment of iMN

The inventors have highlighted that the PLA2R1 epitope profile can change during follow-up and therapeutic treatment of idiopathic membranous nephropathy. Indeed, they showed that anti-CTLD1 and anti-CTLD7 antibodies disappeared with spontaneous or therapeutic disease remission and reappeared with disease relapse while anti-CysR restricted activity was associated with stable and mild disease activity.

The inventors have thus concluded that analysis of the PLA2R1 epitope profile and spreading during follow-up is a powerful tool to monitor disease severity and stratify patients into subgroups with different renal prognosis. The present invention thus provides methods to monitor the progression of idiopathic membranous nephropathy by allowing the clinician to qualitatively and quantitatively measure the degree of autoreactivity for example, by detecting in patient's serum the presence and titers of various anti-PLA2R1 specific autoantibodies targeting the respective antigens CysR, CTLD1 and CTLD7. These autoantibodies are indicative of disease progression.

In particular, the inventors have put in light that the disease is worsened if autoantibodies directed against both CTLD1 and CTLD7 are observed.

"Epitope spreading" refers to the development of immune responses to endogenous epitopes secondary to the release of self antigens during a chronic autoimmune or inflammatory response. Epitope spreading is thus a phenomenon in which new epitopes, within the same or different molecule, are recognized over time by T or B cells from an original non-cross-reactive antigenic site. As described in many autoimmune diseases such as human anti-glomerular basement membrane disease, Pemphigus vulgaris, rheumatoid arthritis, experimental autoimmune encephalomyelitis (EAE), multiple sclerosis, type 1 diabetes and Heymann Nephritis, intra-molecular epitope spreading is associated with worsening of the disease.

The term "epitope" includes any antigenic (e.g., a protein) determinant capable of specific binding to an antibody and/or a T cell receptor. That is, a site on an antigen to which B and/or T cells responds. Epitopic determinants usually consist of chemically active surface groupings of molecules such as amino acids or sugar side chains, and usually have specific three-dimensional structural characteristics, as well as specific charge characteristics. An epitope typically includes at least 3, 5 or 8-10 amino acids. The amino acids may be contiguous, or non-contiguous amino acids juxtaposed by tertiary folding. Conformational and non-conformational epitopes are distinguished in that the binding to the former but not the latter is lost in the presence of denaturing solvents. The anti-PLA2R1 autoantibodies as defined in the context of the present invention all recognize conformational epitopes.

Therefore, in a third aspect, the invention relates to a method for monitoring the effectiveness of a treatment of membranous nephropathy, preferably idiopathic membranous nephropathy, in a subject, comprising:
  determining at a first time point a level of at least one, preferably two, more preferably three autoantibodies selected from the group consisting of autoantibodies respectively directed against CysR, CTLD1 and CTLD7 in a biological sample obtained from said subject at said first time point,
  determining at a second time point a level of at least one, preferably two, more preferably three autoantibodies selected from the group consisting of autoantibodies respectively directed against CysR, CTLD1 and CTLD7 in a biological sample obtained from said subject at said second time point, and
  comparing the levels of autoantibodies of the two time points,
wherein:
  the absence of autoantibodies respectively directed against CTLD1 and CTLD7 or the decrease of the levels of autoantibodies respectively directed against CTLD1 and CTLD7 in the second time point indicates that the treatment is effective; and/or
  the presence of autoantibodies directed against CTLD1 and/or CTLD7 or the increase in the levels of autoantibodies directed against CTLD1 and/or CTLD7 at the second time point indicates that the treatment is not effective.

Preferably, the absence of autoantibodies respectively directed against CysR, CTLD1 and CTLD7 or the decrease of the levels of said autoantibodies in the second time point indicates that the treatment is effective. More precisely, the absence of the autoantibodies respectively directed against CysR, CTLD1 and CTLD7 is an extremely good sign that the treatment is successful and effective.

Said method also allows monitoring of the progression of idiopathic membranous nephropathy.

All the previously disclosed technical data and definitions are applicable here.

An "increased level" or "level higher" or a "decreased level" or a "lower level" than a comparative level, or a "change" or "deviation" or from said comparative level is statistically significant.

An increased level or a decreased level from, or change or deviation from a comparative level can be considered to exist if the level differs from the comparative level by about 5% or more, by about 10% or more, by about 20% or more, or by about 50% or more compared to the comparative level. In the context of the present invention, the "comparative level" preferably refers to the level of autoantibodies obtained at the first time point.

Statistically significant may alternatively be calculated as $P \leq 0.05$. Presence of a marker absent in a control may be seen as a higher level, or change or deviation. Absence of a marker present in a control may be seen as a lower level, or change or deviation.

Current treatment used for treating idiopathic membranous nephropathy can be used on immunosuppressive therapy, as well as symptomatic treatment.

Typically, current treatments used for idiopathic membranous nephropathy especially severe cases of idiopathic membranous nephropathy are immunosuppressive therapy. Said immunosuppressive therapy is typically based on the administration of at least one compound selected from the group consisting of cyclosporin, tacrolimus, azathioprine, infliximab, omalizumab, daclizumab, adalimumab, eculizumab, efalizumab, natalizumab, omalizumab and rapamycin, cyclophosphamide, chlorambucil, and rituximab.

Preferably, the treatment of idiopathic membranous nephropathy is based on the use of cyclophosphamide, chlorambucil, tacrolimus, and rituximab.

Symptomatic treatment is typically based on blockade of the renin-angiotensin system.

The invention thus provides a mean by which a practitioner may predict the reaction of a patient subjected to a treatment.

Typically, the treatment is considered to be effective when a decrease of at least 10%, preferably at least 20%, more preferably at least 30%, even more preferably at least 40%, preferably at least 50%, more preferably at least 60%, even more preferably at least 70%, still even more preferably at least 80%, of the level of the autoantibodies directed against CysR, CTLD1 and CTLD7 is observed. This generally indicates a good prognosis.

Conversely, the treatment is considered to be ineffective when autoantibodies directed against CTLD1 and/or CTLD7 are detected in the second time point whereas they were not at the first point time. Further, the treatment is also considered to be ineffective when level between the first and the second time point is stable or increases by at least 5%, preferably at least 10%, more preferably at least 20%, even more preferably at least 30%, still even more preferably at least 40%, preferably at least 50%, more preferably at least 60%, even more preferably at least 70%, still even more preferably at least 80% or more of the initial level of autoantibodies directed against CTLD1 and/or CTLD7.

Typically, the difference between group based on epitope profile are analysed with the log-rank test, typically using the Prism6 and SAS 9.3 software and p values <0.05 are considered statistically significant.

Several situations may be observed.

In one embodiment, no autoantibodies directed against CTLD1 and/or CTLD7 are detected at the second time point. This indicates that the patient is deemed to be in remission.

In another embodiment, a stable level of autoantibodies directed against CysR is observed at the second time point or the levels obtained at the first and the second time points are comparably similar within statistical analysis variances, with a deviation between about a 1-5% deviation, preferably a 1-3% deviation. This indicates that the patient is deemed to be in remission.

In another embodiment, a stable level of autoantibodies directed against CTLD1 and/or CTLD7 is observed: the levels obtained at the first and the second time points are comparably similar within statistical analysis variances, with a deviation between about a 1-5% deviation, preferably a 1-3% deviation. This indicates a stable disease wherein the treatment has been of insufficient duration (so it should be continued or changed for another type of immunosuppressors if clinically indicated) or is non-effective.

In another embodiment, an increased level of autoantibodies directed against CTLD1 and/or CTLD7 is observed at the second time point compared to the first time point. This indicates a worsening of the disease and/or lack of efficient treatment. An increase of at least 30%, preferably at least 50%, more preferably at least 100%, even more preferably at least 200% is considered to indicate a worsening of the situation and a poor prognosis.

According to the invention, the second time point is chosen later than the first time point. The first and second time points may be strategically chosen, for example with regard to the therapeutic strategy and for the follow-up of a patient who is at risk to develop an idiopathic membranous nephropathy, or who already suffered from a membranous nephropathy, particularly an idiopathic membranous nephropathy, and is at risk to relapse.

For example, the first time point may be before administration of any treatment to the patient and second time point could be placed at a moment when the treatment should show an effect or at the end of treatment, and the assay may be repeated later.

The assay thus may be reproduced several times; the autoantibodies levels may be assessed at more than two time points. Basically, an improvement of the patient health and an effectiveness of treatment are indicated when a global decrease of anti-autoantibodies level is observed during time, especially autoantibodies directed against CTLD1 and/or CTLD7.

Conversely, a degradation of the patient health and an ineffectiveness of treatment are indicated when no decrease of autoantibodies directed against CTLD1 and/or CTLD7 level is observed during time, or when a global increase is observed.

The assay used is identical for all the biological samples collected from the subject at the different time points.

In a case of ineffective treatment, the therapeutic strategy has to be adapted.

Method of Diagnosing Idiopathic Membranous Nephropathy

In a fourth aspect, the invention relates to a method for diagnosing membranous nephropathy, particularly idiopathic membranous nephropathy, in a subject, said method comprising the step a) of detecting in a biological sample obtained from said subject at least one autoantibody selected from the group consisting:
autoantibodies directed against the Cysteine-rich domain (CysR) of PLA2R1; and/or
autoantibodies directed against the C-type lectin domain 1 (CTLD1) of PLA2R1; and/or
autoantibodies directed against the C-type lectin domain 7 (CTLD7) of PLA2R1,
wherein, the presence of one, preferably two and more preferably three from autoantibodies directed against CysR, CTLD1, and/or CTLD7 of PLA2R1 is indicative of membranous nephropathy, preferably idiopathic membranous nephropathy.

In one embodiment, said step a') comprises the following susbteps:
contacting a biological sample obtained from said patient with a PLA2R1, and,
detecting any antigen-antibody complex formed.

In this embodiment, the presence of an antigen-antibody complex formed is indicative of membranous nephropathy, preferably idiopathic membranous nephropathy.

Preferably, said PLA2R1 is selected from the group consisting of human PLA2R1, rabbit PLA2R1 and mouse PLA2R1.

All the previously disclosed technical data are applicable.

As used herein, the term "diagnosis" in all its grammatical forms, refers to the process of identifying a medical condition or an asymptomatic condition. In the context of this invention, the term diagnosis refers to the identification of subjects suffering from idiopathic membranous nephropathy.

Preferably, the methods disclosed herein are in vitro methods

The invention will be further illustrated by the following examples. However, these examples should not be interpreted in any way as limiting the scope of the present invention.

EXAMPLES

Example 1: Epitope Spreading in PLA2R1 is Associated with Bad Prognosis in Membranous Nephropathy Methods Patients Sera of patients with biopsy-proven iMN were collected from five French nephrology centers. iMN was defined by the absence of secondary MN features such as positivity for anti-nuclear antibodies, history of hepatitis B or C, cancer or other immune pathologies (cryoglobulinaemia, sarcoidosis, graft versus host disease, . . . ). Sera from a total of 69 patients were collected, with sequential sera samplings for 16 patients. A poor renal prognosis was defined by proteinuria>4 g/g and/or serum creatinine increase over 30% and/or eGFR<45 ml/min/1.73 $m^2$, as defined by the KDIGO recommendations. Active disease was defined by nephrotic proteinuria>3.5 g/g. Renal failure progression was analyzed after two years of follow-up and was defined by an increase over 30% of serum creatinine from baseline.

Generation and Expression of Membrane-Bound PLA2R1 Deletion Mutants

The inventors generated the series of human PLA2R1 deletion mutants by PCR and cloned them into the pLPCX expression vector (Clontech), as previously described for wild-type human PLA2R1 (GenBank NM 007366). Deletion mutants were generated using the Phusion Site-Directed Mutagenesis Kit (Thermo scientific). All mutants comprised the PLA2R1 signal peptide (Met-1 to Ala-20) and the N-terminal linker sequence (Ala-21 to Trp-35) followed by the PLA2R1 sequence with the following domains deleted at the linker regions: Deletion of the N-terminal domain CysR ($\Delta$C, deletion from Gln-36 to Asp-165), CysR and FNII domains ($\Delta$F, Gln-36 to Thr-223), CysR to CTLD1 domains ($\Delta$1, Gln-36 to Tyr-357), CysR to CTLD2 domains ($\Delta$2, Gln-36 to Ala-504), CysR to CTLD3 domains ($\Delta$3, Gln-36 to Pro-660), CysR to CTLD4 domains ($\Delta$4, Gln-36 to Lys-805), CysR to CTLDS domains ($\Delta$5, Gln-36 to Lys-947), CysR to CTLD6 domains ($\Delta$6, Gln-36 to His-1105), and CysR to CTLD7 domains ($\Delta$7, Gln-36 to Pro-1235). All mutants were generated from a C-terminal HA-tagged (YPYDVPDYA) version of the human full-length PLA2R1 cDNA cloned into the pGEMTeasy vector (Promega). After full sequencing, all deletion constructs were subcloned into the pLPCX retroviral vector and transfected into HEK293 cells using a Ca/PO4 transfection kit (InvitroGen) or Exgen (Biomol GmbH). Expression was confirmed by western blot from transiently transfected HEK293 cell lysates using anti-HA antibodies (see below).

Generation and Expression of Soluble Domains of PLA2R1

Soluble PLA2R1 mutants were generated by PCR as above and cloned into the pcDNA3.1Z-expression vector (LifeTechnologies). They all comprised the PLA2R1 signal peptide followed by the human PLA2R1 sequence coding for the different PLA2R1 domain as followed: CysR domain (CysR, from Ala-21 to Lys-164), CTLD1 domain (CTLD1 or C1, Thr-223 to Asn-359), CTLD2 to CTLD8 (C2C8, 357-Tyr to 1397-Ser), CTLD6 to CTLD8 (C6C8, 947-Lys to 1397-Ser), CTLD6 (C6, 947-Lys to 1114-Pro), CTLD7 (C7, Glu-1097 to 1246-Leu), CTLD8 (C8, Pro-1235 to 1397-Ser), CTLD6 to CTLD7 (C6C7, 947-Lys to 1246-Leu), and CTLD7 to CTLD8 (C7C8, Glu-1097 to 1397-Ser). All soluble mutants were C-terminally HA-tagged. The CysR-FNII-CTLD1 domains were produced and cleaved with thrombin (Sigma) as described by Kao et al, except that the domains were C-terminally HA-tagged. All mutants were expressed in HEK293 cells as described above and cell medium containing the expressed proteins were collected. When proteins were expressed at low levels, medium was precipitated with trichloroacetic acid using standard procedure.

DsbC-His-HA-PLA2R1 fusion proteins were produced in *E. Coli* essentially as described in. The detailed procedure will be published elsewhere. PLA2R1 domains with optimized codons for *E. Coli* expression were added in frame with the leaderless DsbC open reading frame followed by His and HA tags for purification and detection, respectively. Sequences of inserted PLA2R1 domains were: CysR: Ala-26 to Lys-164, CTLD1: Thr-223 to Asn-359, CTLD7: Thr-1102 to Glu-1237, CTLD6-7: 947-Lys to Glu-1237. The 4 single nucleotide polymorphisms (SNPs) variants of CTLD1 were also designed. SNP1: Val-292 and Asp-300, SNP2: Met-292/Asp-300, SNP3: Met-292/His-300 and SNP4: Val-292/His-300.

Western-Blot Analysis

The different deletion mutants and soluble forms of PLA2R1 were analyzed by SDS-PAGE under non-reducing conditions unless indicated otherwise. Total proteins (10-50 μg/well to adjust for the different expression level of each deletion mutant) and cell medium (for transfected soluble forms) were run on 4-15% precast TGX™ Tris-glycine SDS-PAGE gels (Bio-Rad) and transferred to methanol-soaked PVDF membranes (Bio-Rad) under semi-dry conditions using TRANS-BLOT® TURBO™ western blot transfer system (Bio-Rad) at 25 V constant for 12 min. Membranes were blocked overnight at 4° C. in 5% milk with PBS TWEEN® polysorbate nonionic surfactant (PBS-T) 0.05% and then incubated with primary and secondary antibodies for 2 h at room temperature. Primary antibodies were diluted with 0.5% dry milk in PBS-T. Membranes were prepared in multiple replicates and probed with a mouse monoclonal anti-HA antibody (Sigma) at 1:5,000 to validate expression or with the 50 different iMN sera to screen for the epitope profile at a working dilution of 1:25 to 1:500, depending on anti-PLA2R1 titers. Secondary antibody for anti-HA was a goat anti-mouse IgG (Southern Biotech #1030-05) diluted 1:20,000 in PBS-T. IgG secondary antibody for iMN sera was HRP-conjugated mouse anti-human IgG4.

(Southern Biotech #9200-05) diluted 1:30,000 in PBS-T. For anti-PLA2R1 IgG subclass analysis (see supplementary data), we also used a panel of subclass specific anti-IgGs from Southern Biotech and two different anti-total IgGs (Southern Biotech and Santa Cruz). Purified IgGs for validation of IgG subclass specificity were from Fitzgerald. Membranes were washed three times for 5 min in PBS-T after incubation with primary and secondary antibodies. Detection of protein bands was performed with a chemiluminescent substrate (Millipore) and a Fuji LAS3000 imager.

Anti-PLA2R1 ELISA

The anti-PLA2R1 assay was run essentially as described for the standardized and commercially available ELISA. Pure recombinant human PLA2R1 protein corresponding to the entire extracellular domain was coated to ELISA plates in 20 mM Tris pH 8.0 (100 μL/well, 1 μg/mL) at 4° C./overnight. Plates were blocked for 2 h with Seramun-Block (Seramun Diagnostica). Patients' sera were diluted at 1:100 (or higher as needed) in PBS/0.1% dry milk and added in duplicate (100 μL per well) to the ELISA plates, which also contained a serial dilution of an iMN standard serum and a quality control calibrator (between plates). After 2 hours of incubation at room temperature on a plate shaker, plates were washed 4 times with PBS/0.02% TWEEN® 20 polysorbate nonionic surfactant. Anti-human IgG4-horseradish peroxidase conjugate (Southern Biotech #9200-05) diluted 1:7,500 in SeramunStab ST plus was added (100 μL per well) (Seramun Diagnostica) and incubated for 1 h at room temperature on a plate shaker. After four washes, tetramethylbenzidine was added, and the reactions were developed for 15 min and then stopped with HCl 1.2N. The plates were read at 450 nm. Sixty-seven sera from healthy donors were used to defined the normal range, using mean+3 SD. The cut-off was optimized by receiver operating characteristics (ROC) curve analysis. A highly positive index patient serum was used in each plate to generate a standard curve and a negative control.

ELISA Using Soluble Forms of PLA2R1

Plates were coated with anti-HA antibody (Sigma) diluted at 1:5,000 in 20 mM Tris pH 8.0 (100 μL/well) at 4° C./overnight. Plates were then blocked for 2 h with SeramunBlock (Seramun Diagnostica). Cell medium from HEK293 cells transfected with the soluble forms of PLA2R1 (10 to 100 μl/well depending on protein expression) or purified *E. Coli* DsbC-HA-CTLD1 fusion protein (50 ng/well) were then added and incubated for one hour. Plates were washed and patients' sera diluted at 1:100 (or higher as needed) in PBS/0.1% dry milk were added in duplicate (100 .mu·L per well) to the ELISA plates, which also contained a serial dilution of an iMN standard serum and a quality control calibrator (between plates). After 2 hours of incubation at room temperature on a plate shaker, plates were washed 4 times with PBS/0.02% TWEEN® 20 polysorbate nonionic surfactant. Anti-human IgG4-horseradish peroxidase conjugate (Southern Biotech #9200-05) diluted 1:7,500 in SeramunStab ST plus was added (100 μL per well) (Seramun Diagnostica) and incubated for 1 h at room temperature on a plate shaker. Subclass analyses were performed with specific anti-IgGs as indicated above. After four washes, tetramethylbenzidine was added, and the reactions were developed for 15 min and then stopped with HCl 1.2N. The plates were read at 450 nm. Twenty sera from healthy donors were used to defined the normal range, using mean+3 SD. The cut-off was optimized by receiver operating characteristics (ROC) curve analysis. A highly positive index patient serum was used in each plate to generate a standard curve and a negative control.

An ELISA Index value for each antigen was obtained for patients or normal subjects as follows (mean test result−mean domain negative control)/(mean domain positive control−mean domain negative control)×domain correction factor×100. The domain correction factor was determined for each domain as mean of all the positive controls for that domain on all plates minus the mean of the negative controls, divided by the cut-off for that domain assay as described by Warren et al. 2003.

Statistical Analyses

For descriptive statistics, data are presented as mean±standard deviation (for variables with Gaussian distribution) or median (ranges) (for variables with non Gaussian distribution). The inventors used the Shapiro-Wilk test to determine if a variable has a Gaussian distribution. Qualitative criteria were compared using Chi-square test or Fisher's exact test according to the terms of use. Quantitative variables were compared using the Student t-test or Wilcoxon-Mann-Whitney test (for variables with non Gaussian distribution) and for multiple comparisons using the ordinary One-way Anova (for variables with Gaussian distribution), Kruskal-Wallis (for variables with non Gaussian distribution) and Turkey's test (for comparison two by two). A poor prognosis was defined at LOCF as defined by KDIGO by a proteinuria>4 g/g and or serum creatinine increased over 30% and/or eGFR<45 ml/min/1.73 m². Survival curves for renal survival were calculated using Kaplan-Meier estimates for survival distribution. The endpoint for renal survival analysis was the time where we measured an increase over 30% of serum creatinine from baseline. Differences between groups based on epitope profile were analyzed with the log-rank test. Multivariable cox regression analysis was performed. In the analysis, we included and adjusted for all clinical parameters that might influence the prognosis (age, sex, proteinuria, creatinemia, immunosuppressive treatment and anti-PLA2R1 titer). Hazard ratios are expressed per natural logarithm unit of PLA2R1 antibody level measured by ELISA and are dichotomized for sex, treatment and different domains group. All statistics were performed using Prism6 and SAS 9.3 softwares. P-values <0.05 were considered as statistically significant.

RESULTS

Identification of Three Epitope Profiles

The inventors first generated by site-directed mutagenesis a series of 9 deletion mutants of PLA2R1, in which the inventors successively deleted each domain from the N-terminal sequence, thus leaving the receptor membrane-bound. The inventors introduced in the cytoplasmic tail a small HA tag which allowed us to validate the expression of the recombinant proteins in HEK293 cells. All PLA2R1 constructs were readily expressed except for Δ6 which was poorly detected with anti-HA antibodies, but was clearly detected by some patients. They then screened sera from 50 iMN patients with anti-PLA2R1 antibodies for their reactivity against the wild-type protein versus deletion mutants. They chose to screen patients for IgG4 anti-PLA2R1 subclass because many studies have shown that IgG4 is the predominant IgG subclass in iMN, correlating the most with disease activity. Successive deletion of CysR, CTLD1 and CTLD7 led to the progressive loss of PLA2R1 recognition for 12, then 11 and 27 more patients, identifying three epitope profiles that likely correspond to distinct epitopes in each of these three domains.

CysR and CTLD1 Domains Contain Distinct Epitopes Recognized by Two Different Anti-PLA2R1 Autoantibodies Fresquet et al recently described that the CysR domain alone contains an anti-PLA2R1 epitope while Kao et al suggested that one or several epitopes are intertwined between CysR and CTLD1 domains. Our above data rather suggest the presence of two independent epitopes in CysR and CTLD1 domains. To confirm this hypothesis, the inventors designed 4 constructs driving the expression of HA-tagged soluble forms of CysR and CTLD1 domains alone, in either HEK293 cells or *E. coli*. The inventors also prepared the two constructs described by Kao et al. in which the three domains CysR, FNII and CTLD1 are expressed together (triple domain), with insertion of a thrombin protease site either at the linker region between CysR and FNII or between FNII and CTLD1. Expression of CTLD1 alone in HEK293 cells was very low (not shown), consistent with previous data from Kao et al. On the other hand, the CysR domain alone was expressed in HEK293 cells at low but significant levels, consistent with data from Fresquet et al. To circumvent the weak expression of the two single domains in HEK293 cells, we produced them in *E. Coli* as HA-tagged DsbC fusion proteins and purified soluble and folded CysR and CTLD1 proteins. The inventors could then easily detect the proteins by western blot under non reducing conditions with anti-HA antibodies. As for the two constructs from Kao et al, only the first construct with a thrombin site between CysR and FNII was well expressed in HEK 293 cells and could be detected with anti-HA before and after cleavage with thrombin. Of importance, the band labeled with anti-HA after cleavage correspond to the cleaved FNII-CTLD1-HA domain and not the cleaved CysR domain which has no HA tag. In summary, 4 constructs could be obtained and validated by western blot with anti-HA antibodies: the CysR domain alone and the CysR-FNII-CTLD1 triple domain expressed in HEK293 cells, as well as the CysR and CTLD1 domains expressed as single domains in E. coli. The inventors then tested sera from patient 1 with a CysR profile and from patients 2 and 3 with a CTLD1 profile against these constructs, with the triple domain cleaved or not by thrombin. Serum from patient 1 could only recognize constructs containing the CysR domain, and only when expressed alone as a DsbC fusion protein or as a triple domain, but not after cleavage with thrombin or when the CysR-HA domain is loaded alone. In fact, the CysR-HA domain could be detected with the anti-HA antibody under reducing conditions but not under reducing conditions, suggesting that the CysR domain is not hydrophobic enough by itself to properly transfer to western blot PVDF membranes in our conditions (similar results were observed on nitrocellulose membranes), and hence cannot be detected by patients' anti-CysR antibody. On the other hand, serum from patients 2 and 3 could recognize constructs containing both the CTLD1 domain and the CysR domains expressed alone as DsbC fusion proteins or as a triple domain, now cleaved or not with thrombin for the FN-CTLD1 domain. Interestingly, the relative signals against the two domains were different, likely because of different titers for each anti-CysR and anti-CTLD1 autoantibodies in the two patients' sera. To confirm these results, the inventors set-up an ELISA in which they took advantage of the HA-tag present in all antigens to affinity capture them into wells precoated with anti-HA antibody. No signal was obtained when anti-HA or antigens were omitted in all conditions. The ELISA data were in perfect accordance with the western blots and were much more sensitive and quantitative. As expected, patient 1 recognized the CysR and the CysR-FNII-CTLD1 triple domain not cleaved with thrombin but neither the CTLD1 domain expressed alone nor the CysR-FNII-CTLD1 triple domain efficiently cleaved with thrombin that in fact generates a free CysR domain that cannot bind to anti-HA-coated well and is washed away while the corresponding FNII-CTLD1-HA domain will bind to the well. The inventors inferred from the western blots that sera from patients 2 and 3 have two different autoantibodies directed against different epitopes in CysR and CTLD1 domains, with likely higher titer to CysR for patient 2 and higher titer to CTLD1 for patient 3. The ELISA data clearly confirmed this view, with higher signal on CysR than CTLD1 and no signal on the triple domain after thrombin cleavage for patient 2 and results in mirror for patient 3. To even further demonstrate the presence of two different autoantibodies targeting CysR or CTLD1, the inventors performed i) depletion experiments in which we pre-absorbed the serum of patient 2 (containing CysR and CTLD1 autoantibodies) onto anti-HA beads loaded with either CysR or CTLD1 domains and analyzed the flow-through fraction for reactivity in western blot again loaded with CysR and CTLD1 domains; and ii) competition experiments in which we pre-incubated the serum of patient 2 with an excess of CysR or CTLD1 domains from E. coli and then probed the serum in a western blot loaded with CysR and CTLD1 domains.

Finally, the inventors performed competition experiments with the CysR, CTLD1 and CTLD6-7 domains expressed in E. coli against full-length PLA2R1 by ELISA and observed data fully in line with the above results. The CysR antigen could fully block the ELISA signal for sera of two patients with a CysR profile but only partially for sera from two other patients with a CTLD1 profile. In line with this, competition with the CTLD1 antigen did not inhibit the signal for the CysR sera but partially inhibited that of the CTLD1 sera while the combination of the two antigens fully inhibited the PLA2R1 signal. Finally, addition of CTLD67 had no effect by itself, demonstrating that this antigen cannot interfere with the interaction of anti-PLA2R1 antibodies targeting the CysR and CTLD1 domains. Together, this series of experiments clearly demonstrate the presence of two autoantibodies, with one recognizing CysR and the other recognizing CTLD1. The experiments also very clearly show that CysR and CTLD1 domains exhibit distinct epitopes which can be independently recognized by the two different autoantibodies, these latters being present at different titers in different patients' sera. They also produced the DsbC-HA-CTLD1 domains with the 4 possible combinations of SNPs previously described and did not observe a difference in signal with sera from two patients with either a CTLD1 or a CTLD7 profile. The inventors also performed western blots under reducing versus non reducing conditions and demonstrate that the reactivity of anti-PLA2R1 antibodies towards CysR and CTLD1 is dependent on the disulfide bonds present in these domains.

CTLD7 Contains a Third Epitope Recognized by Anti-PLA2R1 Antibodies

To confirm the inital results suggesting a third, more distal epitope in the PLA2R1 extracellular region, and also demonstrate that this epitope is independent of the other domains of PLA2R1, we designed a series of soluble forms of PLA2R1 deleted from the CysR, FNII and CTLD1 domains. The inventors prepared a total of 8 constructs converging towards CTLD7: CTLD2 to CTLD8 (C2C8), CTLD2 to CTLD6 (C2C6), CTLD6 to CTLD8 (C6C8), CTLD6 to CTLD7 (C6C7), CTLD6 (C6), CTLD7 (C7), CTLD7 to CTLD8 (C7C8) and finally CTLD8 (C8). All these constructs had a HA-tag and the inventors could confirm their expression in HEK293 cells by western blot with anti-HA antibody under reducing conditions. However, the detection with anti-HA under non reducing conditions was more difficult, especially for the short soluble forms narrowing down to CTLD7, likely because the CTLD7 and its neighboring domains are highly polar (probably due to the high glycosylation as evidenced from the migration of the soluble forms) and do not transfer well under non reducing conditions (not shown). This view likely explains the fact that patient 4 who had a CTLD7 profile could recognize C2C8 and C6C8 soluble forms but not the shorter constructs. Nonetheless, the fact that this patient recognizes C2C8 and C6C8 which are devoid of CysR and CTLD1 domains clearly demonstrates that C6C8 contains a third anti-PLA2R1 epitope independent of CysR and CTLD1. To overcome this problem of transfer, the inventors probed the different soluble constructs using the anti-HA ELISA assay as performed above for CysR and CTLD1. They observed that all the constructs containing a CTLD7 domain and even CTLD7 alone were well recognized by the sera from patients 4 and 5 with a CTLD7 profile. As a negative control, the inventors used serum from patient 1 that as expected did not recognize any of the constructs. Together, these data demonstrate the presence of a third independent epitope in CTLD7 with a corresponding autoantibody only present in sera from patients with a CTLD7 profile. As above for CysR and CTLD1, the inventors performed western blots under reducing versus non reducing conditions and demonstrate that the reactivity of anti-PLA2R1 antibodies towards CTLD7 is dependent on the disulfide bonds present in this domain.

Set-Up of Three Specific ELISAs with CysR, CTLD1 and CTLD7 as Antigens

Based on the above results, the inventors set-up three ELISAs to specifically measure autoantibodies targeting the CysR, CTLD1 and CTLD7 domains. They used as antigens the CysR domain produced in HEK293 cells, the CTLD1 domain produced in E. coli and the CTLD6-7 construct produced in HEK293 cells, as this latter was easier to produce in large scale than CTLD7 alone. As above, the two antigenic domains produced in HEK cells were HA-affinity captured on ELISA plates pre-coated with anti-HA antibody while the CTLD1 domain from E. coli could be directly coated or captured with anti-HA. Adsorbed antigens were then incubated with patients' sera followed by detection with a secondary anti-IgG4 antibody coupled to peroxidase. The inventors validated the three ELISAs and measured the epitope-specific titers using a cohort of 69 PLA2R1-positive iMN patients (Table 1 below) versus 20 healthy donors. The cohort of 69 iMN patients comprised the 50 sera screened and 19 additional cases.

TABLE 1

Clinical characteristics of patients enrolled in this study

| | |
|---|---|
| Age at diagnosis (years) | 55 ± 15 |
| Gender (Male/Female) | 54/15 |
| Proteinuria on diagnosis (g/g) | 5.0 (1.4-24.0) |
| Serum creatinine at diagnosis (µmol/L) | 99 (43-385) |
| Months between diagnosis and PLA2R1 assay | 0 (0-100) |
| Anti-PLA2R1 titer (ELISA Index Value) | 3241 (210-50817) |
| Proteinuria at PLA2R1 assay (g/g) | 4.0 (0.3-24.0) |
| Serum creatinine at PLA2R1 assay (µmol/L) | 94 (43-600) |
| Patients treated before PLA2R1 assay[1] | 6 (9%) |
| Patients treated during follow-up[1] | 41 (59%) |
| LOCF[2] (months) | 36 (12-216) |
| Proteinuria at LOCF (g/g) | 2.0 (0.0-20.0) |
| Serum creatinine at LOCF (µmol/L) | 119 (48-926) |
| Spontaneous remission[3] | 18 (26%) |
| Poor prognosis at LOCF[4] | 31 (45%) |
| Hemodialysis[8] | 12 (17%) |

Normal values are mean ± standard deviation; non normal values are median (ranges); qualitative values are number (%).
[1]Treated with immunosuppressive treatment. All patients received symptomatic treatment.
[2]LOCF: Last Observation Carried Forward.
[3]Spontaneous remission is defined by remission induced by symptomatic treatment (RAS blockers and diuretics) without immunosuppressive treatment.
[4]Poor renal prognosis at LOCF is defined by proteinuria > 4 g/g and/or serum creatinine increased over 30% and/or eGFR < 45 ml/min/1.73 m². Patients with ESKD on hemodialysis.

All patients were clinically well characterized and positive for anti-PLA2R1 by ELISA using full-length PLA2R1 as antigen (Table 1). Most patients had nephrotic range proteinuria (urinary protein/creatinine ratio (UACR) over 3.5 g/g) at diagnosis (74%) and were naive of immunosuppressive treatment (91%) at the time of PLA2R1 assays by ELISA and western blot. Patients had a mean follow-up of 36 months from PLA2R1 assays. All patients received symptomatic treatment. Eighteen patients entered into remission under RAS-blockade. Thirty-six patients received an immunosuppressive treatment and 21 entered into remission. The inventors analyzed their renal outcome and defined a poor renal prognosis according to KDIGO as persistence of UACR>4.0 g/g and/or serum creatinine increase over 30% and/or estimated glomerular filtration rate (eGFR using the simplified MDRD formula)<45 ml/min/1.73 m² at last observation carried forward (LOCF). Thirty-one patients had a poor renal outcome at the end of the follow-up including 12 patients with end-stage kidney disease (ESKD). They also analyzed renal survival 24 months after anti-PLA2R1 assay and defined an event by an increase over 30% of serum creatinine from baseline (Table 1).

All but one sera (n=68) recognized the CysR domain by ELISA. Forty-two sera recognized the CTLD1 domain and 32 sera recognized the CTLD7 domain. They then classified patients into three groups based on their ELISA pattern.

Twenty-three patients were classified in a group referred to as "the CysR group" as they had only antibodies targeting the CysR domain.

Fourteen patients were classified under a group referred to as "the CysRC1 group", with 13 having activities against both the CysR and CTLD1 domains, and one having antibodies only against CTLD1.

Thirty-two patients were finally classified into a group referred to as "the CysRC1C7 group", with 28 having antibodies targeting the three domains CysR, CTLD1 and CTLD7 and 4 patients targeting CysR, CTLD7 but not CTLD1.

When considering the 50 patients initially screened by western blot, the inventors observed a perfect concordance between the ELISA data and their western blot epitope profiles. Finally, the inventors observed that the CysR titer was significantly higher in the CysRC1 and CysRC1C7 groups than in the CysR. On the other hand, no difference was observed for the CTLD1 titer between CysRC1 and CysRC1C7 groups.

Clinical Characteristics of Patients with the Three Epitope Profiles

The inventors compared the clinical characteristics of patients of the three groups: CysR, CysRC1 and CysRC1C7 (Table 2).

TABLE 2

Comparison of clinical characteristics and follow-up of patients stratified according to their epitope profiles.

| Patients[2] | Group CysR n = 23 | Group CysRC1 n = 14 | Group CysRC1C7 n = 32 | p value[3] |
|---|---|---|---|---|
| Age at diagnosis (years) | 48 +/− 12 | 54 +/− 16 | 61 +/− 15 | 0.008 |
| Gender (Male/Female) | 19/4 | 10/4 | 25/7 | ns |
| Proteinuria on diagnosis (g/g) | 3.7 (2.0-10.8) | 4.7 (1.4-15.0) | 6.0 (2.5-24.0) | ns |
| Serum creatinine at diagnosis (µmol/L) | 93 (54-134) | 96 (43-150) | 103 (59-385) | ns |
| Months between diagnosis and PLA2R1 assay | 0 (0-36) | 1 (0-84) | 0 (0-100) | ns |
| Anti-PLA2R1 assay (ELISA Index Value)[1] | 3175 (394-8043) | 1625 (367-5947) | 4288 (210-50817) | ns |
| Proteinuria at PLA2R1 assay (g/g) | 3.0[4] (0.3-5.1) | 3.0 (0.8-10.6) | 5.0[4] (0.3-24.0) | 0.018 |
| Serum creatinine at PLA2R1 assay (µmol/L) | 92 (45-149) | 96 (43-280) | 100 (59-926) | ns |
| Patients treated before PLA2R1 assay[4] | 3/23 | 2/14 | 1/32 | ns |
| Patients treated during follow-up[5] | 12/23 | 8/14 | 21/32 | ns |

TABLE 2-continued

Comparison of clinical characteristics and follow-up of patients stratified according to their epitope profiles.

| Patients[2] | Group CysR n = 23 | Group CysRC1 n = 14 | Group CysRC1C7 n = 32 | p value[3] |
|---|---|---|---|---|
| LOCF[5] (months) | 36 (12-201) | 44 (12-133) | 33 (12-216) | ns |
| Proteinuria at LOCF (g/g) | 0.6[4] (0.0-5.0) | 2.0 (0.0-10.6) | 5.0[4] (1.0-20.0) | 0.01 |
| Serum creatinine at LOCF (μmol/L) | 89 (55-181) | 130 (57-297) | 157 (48-600) | ns |
| Spontaneous remission[6] | 10/23 43% | 4/14 29% | 4/32 12% | 0.03 |
| Hemodialysis[7] | 0/23 (0%) | 2/14 (14%) | 10/32 (31%) | 0.01 |

[1]Epitope profile and anti-PLA2R1 ELISA assays were performed on the same serum sample.
[2]Normal values are mean ± standard deviation; non normal values are median (ranges); qualitative values are number (%).
[3]ANOVA or Kruskal-Wallis tests for continuous (for Gaussian or non Gaussian distribution, respectively) variables and Chi-square or Fisher's exact tests for categorial variables.
[4]Treated with immunosuppressors. All patients received symptomatic treatment.
[5]LOCF: Last Observation Carried Forward.
[6]Spontaneous remission is defined by remission induced by symptomatic treatment (RAS blockers and diuretics) without immunosuppressive treatment.
[7]Patients with ESKD on hemodialysis.

There was no statistically significant difference between the three groups for sex, number of patients with immunosuppressive treatment and titers of anti-PLA2R1 antibodies measured by ELISA using full-length PLA2R1. In contrast, they observed a significant difference for age: patients in the CysR group were significantly younger than patients from CysRC1 and CysRC1C7 groups (p=0.008; using the ordinary One-way Anova test). The mean age at presentation was 48 years old for the CysR group, 54 years old for the CysRC1 group and 61 years old for the CysRC1C7 group.

Proteinuria at the time of PLA2R1 testing was significantly lower in the CysR group (Table 2, p=0.018; using Kruskal-Wallis test). The inventors then classified patients based on their UACR at serum sampling into three subgroups: below 3 g/g (n=22), between 3 to 5 g/g (n=22) and over 5 g/g (n=25), and compared their ELISA titers measured with full-length PLA2R1, CysR, CTLD1 and CTLD7 antigens. Only anti-CTLD7 titers were significantly higher in the group with UACR over 5 g/g compared to the two other groups (p=0.006 using Kruskal-Wallis test). Furthermore, they observed a progressive increase of CTLD7 titer with increasing proteinuria.

Evolution of Patients in the Three Epitope Groups

In our cohort, all patients received a symptomatic treatment with RAS-blockade and/or diuretics, and 41 patients received an immunosuppressive treatment (59%). The use of immunosuppressive treatments and the median follow-up were not different between the three epitope groups (n=0.6 using Chi-square test and p=0.24 using Kruskal-Wallis test, respectively).

In the CysR group (n=23), among the 12 patients who received an immunosuppressive treatment, 10 achieved remission defined by a UACR lower than 4 g/g with a eGFR over 45 ml/min/1.73 m$^2$ and only two had a poor renal prognosis at the end of follow-up (UACR>4 g/g or eGFR<45 ml/mn/1.73 m$^2$). Among the 11 patients who did not receive any immunosuppressive treatment, 10 entered into remission and one patient who already had a significant renal failure at presentation had poor prognosis at LOCF.

In the CysRC1 group (n=14), among the eight patients treated with immunosuppressive therapy, three entered into remission and five presented a poor renal prognosis (one patient developed ESKD). Among the six patients who did not receive any immunosuppressive treatment, four reached remission and two had a poor renal prognosis (one patient entered into ESKD). In this group, 50% of patients had a poor renal prognosis.

In the CysRC1C7 group (n=32), among the 21 patients who received immunosuppressive treatment, eight achieved remission (38%) and 13 had a poor renal prognosis at LOCF including seven patients with ESKD. Among the 11 patients who did not received immunosuppressive treatment, seven already had renal failure at presentation and four entered in spontaneous remission.

In the CysR group, the inventors observed more spontaneous remission (p=0.03 using Chi-square test). ESKD developed in two and 10 patients in respectively CTLD1 and CTLD7 groups, but in none of the patients of the CysR group (p=0.01 using Chi-square test).

Finally, a survival curve analysis without serum creatinine increase over 30% from baseline after 2 years of follow-up showed a striking increase of renal failure progression for patients in the CysRC1 and CysRC1C7 groups compared to the CysR group (p=0.0025 using Log-rank test). Renal failure progression was also significantly slower in patients with a CysR profile in the subgroup of 33 patients who received an immunosuppressive treatment (p=0.014 using Log-rank test).

Identification of Prognostic Factors

As summarized in Table 3, patients were divided into a remission group (n=38) and a poor renal prognosis group (n=31) at the end of follow-up according to KDIGO guidelines (UACR>4 g/g or eGFR<45 ml/min/1.73 m$^2$).

TABLE 3

Clinical baseline characteristics, epitope profile and PLA2R1 antibody level of patients reaching remission and bad prognosis at last observation carried forward

| | Remission n = 38 | Bad prognosis n = 31 | p value univariate |
|---|---|---|---|
| Sex | 9 F/29 M | 6 F/25 M | ns |
| Age | 50 +/- 2.2 | 62 +/- 2.6 | 0.0006 |
| Proteinuria at diagnosis (g/g) | 4.45 (1.4-15.0) | 5.2 (2.5-24.0) | ns |
| Creatinemia at diagnosis (μmol/L) | 88 (43-187) | 113 (60-385) | 0.0002 |
| Follow-up (months) | 36 (12-216) | 30 (12-158) | ns |
| Patients on immunosuppressive treatment | 21 (55%) | 20 (64%) | ns |
| Group CysR | 20 (52%) | 3 (10%) | 0.0002 |
| Group CysRC1 | 7 (18%) | 7 (23%) | ns |
| Group CysRC1C7 | 11 (30%) | 21 (67%) | 0.0013 |
| PLA2R1 titer | 2594 (210-44194) | 5947 (424-50817) | 0.04 |

Normal values are mean ± standard deviation; non normal values are median (ranges); qualitative values are number (%).
At the end of the study, 38 patients reached remission and 31 had bad prognosis (Proteinuria > 4 g/g and/or serum creatinine increased over 30% and/or eGFR < 45/ml/min/1.73 m$^2$.
Patients with bad prognosis at the end of the follow-up were significantly older, had higher creatinine level at diagnosis, were not in CysR Group but much more in CTLD7 Group and had higher PLA2R1 antibody level. There was no difference in sex ratio, proteinuria at diagnosis, time of follow-up, in the percentage of patients who received immunosuppressive therapy and CTLD1 group between patients with bad and good prognosis.

There were no significant difference in age, proteinuria at diagnosis, mean follow-up and percentage of patients receiving immunosuppressive therapy between the two groups at time of inclusion. As described in other studies, age and serum creatinine levels at diagnosis were higher in the group who did not reach remission (p=0.0006 and p=0.0002 using unpaired t-test and Mann-Whitney test respectively). The ELISA titers for full-length PLA2R1, CysR, CTLD1 and CTLD7 specific assays were all significantly higher in the group with a poor renal prognosis, and more particularly for CTLD1 and CTLD7 specific assays (p=0.04, p=0.03, p=0.003 and p<0.0001, respectively; Mann-Whitney test). A multiple Cox regression analysis identified CysRC1 and CysRC1C7 groups and a high titer with full-length PLA2R1 as independent risk factors for a poor renal prognosis. The epitope profiling is thus a prognostic factor for the onset of subsequent renal events.

Epitope Spreading During Follow-Up

The inventors also had 16 patients with sera available during follow-up. They searched for switches in PLA2R1 epitope profile during the course of the disease. Nine patients had stable epitope profiles during follow-up with stable disease activity, including five with stable or decreasing anti-CysR restricted activity after immunosuppressive treatment or symptomatic treatment and who entered into remission. Patient 9 remained in remission during 14 years after kidney transplantation and under cyclosporine treatment while he had high ELISA titers measured with the full-length PLA2R1. This patient had only activity against CysR with no intra-molecular spreading. Two biopsies in May 1997 and May 2011 confirmed the presence of immune deposits at the time of recurrence and 14 years after. Two patients had a stable CTLD1 profile with active disease. Two patients had a stable CTLD7 epitope profile and were in active disease.

Four patients switched their epitope profile with a modification of disease activity. One patient from the CysRC1C7 group switched to the CysR group and entered into remission under immunosuppressive treatment. Inversely, two patients switched from CysR to the CysRC1 and CysRC1C7 groups and relapsed with nephrotic proteinuria and the last patient had positivity against CysR and CTLD7 with active disease and became also positive against CTLD1 after 2 years with increased proteinuria.

Finally, three patients presented a progressive decreasing of all three antibodies against each domain and entered into remission.

IgG Subclasses

All of the above epitope studies were designed to measure IgG4 anti-PLA2R1 antibodies, as there is a large body of evidence that IgG4 and anti-PLA2R1 IgG4 play a more prominent role in iMN pathogenesis. To confirm this view, the inventors compared the reactivity of sera from patients selected from the three epitope groups by western blot on the deletion mutants of PLA2R1 and by ELISA on CysR, CTLD1 and CTLD7 antigens with detection for the different IgG subclasses (1, 2, 3 and 4) and total IgGs. To ascertain our results, the inventors validated the specificity of IgG subclass detection with purified IgGs and then performed western blot assays and ELISAs with simultaneous detection for all IgGs. In addition to anti-PLA2R1 IgG4 antibodies, the inventors observed in some patients the presence of IgG1, IgG2 and IgG3 anti-CysR and anti-CTLD1 autoantibodies. However, the inventors never observed anti-CTLD7 autoantibodies different from IgG4. Finally, the pattern observed with total IgG by western blot was quite similar to that of IgG4. All together, these results indicate that the choice to detect anti-PLA2R1 IgG4 was likely the most powerful, and with most likely no change in the patients' epitope classification if we were choosing detection with total IgGs.

Discussion

The inventors screened 69 patients with iMN disease and identified epitopes in three domains of PLA2R1: Cys-R, CTLD1 and CTLD7. Interestingly, several common genetic variants associated with iMN have been localized in these domains. Our results further extend those by Kao et al. and Fresquet et al. who identified epitopes in the CysR-CTLD1 region and CysR alone, respectively. The data clearly shows that CysR and CTLD1 are two independent domains recognized by distinct anti-PLA2R1 antibodies. The ability to identify CTLD7 as an additional domain and more clearly identify CysR and CTLD1 as two separate epitopes is likely due to the facts that the inventors generated a different and full set of PLA2R1 deletion mutants and also screened a large number of patients with IgG4 detection which is more sensitive than total IgG. Indeed, the two previous studies only used a very limited number of patients or used a pool of 5 patients' sera, and then performed competition assays with more patients. Furthermore, it was unclear whether sera were collected from patients with active disease or in remission.

The inventors then observed that anti-PLA2R1 reactivity against CysR at serum sampling was associated with favorable outcome while reactivity against CTLD1 and CTLD7 was associated with active disease and poor renal prognosis. Furthermore, the inventors showed that the epitope profiles can change during follow-up. Anti-CTLD1 and anti-CTLD7 antibodies disappeared with disease remission and reappeared with disease relapse while anti-CysR restricted activity was associated with stable and mild disease activity. Importantly, all patients still had anti-PLA2R1 activity when measured by ELISA with full-length PLA2R1 (Table 1). These findings may explain the discrepancies observed between the level of disease activity and the anti-PLA2R1 titers.

These findings led the inventors to hypothesize that anti-PLA2R1 antibodies may be initially raised against the N-terminal CysR domain with pauci-symptomatic iMN disease: patients in the CysR group are younger than the other groups suggesting that these patients are probably at the beginning of the disease. A second immune challenge (allergy, infection . . . ) might then induce intra-molecular spreading in PLA2R1 towards the C-terminal end (CTLD1 or CTLD7) leading to more active disease. Epitope spreading is a phenomenon in which new epitopes, within the same or different molecule, are recognized over time by T or B cells from an original non-cross-reactive antigenic site. As described in many autoimmune diseases such as human anti-glomerular basement membrane disease, Pemphigus vulgaris, rheumatoid arthritis, experimental autoimmune encephalomyelitis (EAE), multiple sclerosis, type 1 diabetes and Heymann Nephritis, intra-molecular epitope spreading is associated with worsening of the disease. Moreover, intra-molecular epitope spreading may also modulate remission and relapse of iMN. As described in EAE, epitope spreading plays a major role in disease progression in mice, and short-term co-stimulation blockade can specifically inhibit initiation of the T cell response, preventing epitope spreading and worsening of the disease.

In conclusion, the results show that three PLA2R1 domains are involved in anti-PLA2R1 binding, with two of them more closely associated with active iMN and likely linked by a mechanism of epitope spreading.

Example 2: Use of Murine PLA2R1 for Assessing the Outcome of Patients Suffering from iMN The inventors have shown that the specific detection of a subset of anti-PLA2R1 autoantibodies using the mouse PLA2R1 ELISA can predict long-term clinical outcome. For this purpose, the inventors have first measured the IgG4 anti-PLA2R1 titers in 41 iMN patients at the time of first serum sample analysis versus controls with the hPLA2R1 (human), rbPLA2R1 (rabbit) and mPLA2R1 (mouse) ELISAs. They tested the cross-reactivity of all 41 iMN sera at the time of first serum sampling towards the three PLA2R1 orthologs first by WB, then using antigen-specific ELISAs. All sera that recognized hPLA2R1 in WB analysis also recognized rbPLA2R1, but only 26 out of 41 patients reacted to mPLA2R1.

To confirm these results and quantitatively determine the levels of anti-PLA2R1 autoantibodies, they measured the same sera with the ortholog-specific ELISAs. Toward this goal, the inventors set up another ELISA for mPLA2R1 using a recombinant soluble form of mPLA2R1 comprising the full-length extracellular domain, as for rbPLA2R1 and hPLA2R1. They thus validated this recombinant form of mPLA2R1 by WB and sPLA2 binding assay.

As for hPLA2R1 and rbPLA2R1, the mPLA2R1 ELISA was specific for iMN patients and did not recognize any other disease or healthy controls. All 41 iMN sera reacted in hPLA2R1 and rbPLA2R1 ELISAs, but only 32 of them (78%) had activity in the mPLA2R1 ELISA. Furthermore, in contrast to hPLA2R1 and rbPLA2R1 ELISAs, only a few iMN sera gave a high titer in the mPLA2R1 ELISA.

The inventors then analyzed the association between age, gender, proteinuria, serum creatinine, immunosuppressive treatment as well as human, rabbit and mouse PLA2R1 antibody titers at first serum sampling and the clinical outcome of the patients, ie those with bad prognosis versus those in remission. Only the anti-mPLA2R1 activity was significantly associated with persistent active disease in both univariate (p=0.007) and multivariate analyses (p=0.009). A ROC curve analysis of the mPLA2R1 ELISA titers defined a threshold of 605 RU/mL above which 100% of patients (12 patients) had a poor prognosis (100% specificity, 57% sensitivity, AUC 0.76, p=0.004, 95% IC 0.60-0.91).

Accordingly, analysis of renal outcome by the Kaplan-Meier method showed that patients with high titers of anti-mPLA2R1 antibodies had poor renal outcome. Indeed, patients with anti-mPLA2R1 antibody titers above 605 RU/mL (n=12) had a higher rate of doubling of serum creatinine (p<0.001 using the log-rank test) than patients with anti-mPLA2R1 antibody titer below 605 RU/mL (n=29). ROC curves could not identify such a threshold for hPLA2R1 and rbPLA2R1 antibody titers and the corresponding subgroups of 12 patients with highest anti-hPLA2R1 or anti-rbPLA2R1 titers did not have a statistically significant poor renal outcome compared to the remaining patients (p=0.88 and p=0.21, respectively).

These results indicate that rbPLA2R1 is an alternative antigen to hPLA2R1 to measure anti-PLA2R1 in active disease while mPLA2R1 is a unique antigen that can detect a subset of anti-PLA2R1 autoantibodies present at high levels (>605 RU/mL) only in iMN patients at risk of poor prognosis, and thus is useful to predict iMN outcome.

The invention claimed is:

1. A method for monitoring the effectiveness of a treatment of membranous nephropathy or idiopathic membranous nephropathy in a human subject, comprising:
  obtaining at a first time point a first body fluid sample selected from the group consisting of blood, serum and plasma;
  detecting in vitro a first level of at least one, two, or three autoantibodies selected from the group consisting of an autoantibody directed against cysteine-rich domain (CysR) of PLA2R1, an autoantibody directed against C-type lectin domain 1 (CTLD1) of PLA2R1, and an autoantibody directed against C-type lectin domain 7 (CTLD7) of PLA2R1, in said first body fluid sample obtained from said human subject at said first time point;
  obtaining at a second time point a second body fluid sample selected from the group consisting of blood, serum and plasma, wherein said first body fluid sample and said second body fluid sample are from a same body fluid;
  detecting in vitro a second level of said at least one, two, or three autoantibodies selected from the group consisting of an autoantibody directed against CysR of PLA2R1, an autoantibody directed against CTLD1 of PLA2R1, and an autoantibody directed against CTLD7 of PLA2R1, in said second body fluid sample obtained from said human subject at said second time point, and
  comparing the first and second levels of autoantibodies, wherein:
    absence, from the second body fluid sample obtained from the subject at the second time point, of detectable autoantibodies respectively directed against CTLD1 and CTLD7, or a decrease of the second level of autoantibodies respectively directed against either or both of CTLD1 and CTLD7 relative to the first level, indicates that the treatment being monitored is effective; and
  continuing the treatment being monitored; or
    presence, in the second body fluid sample obtained from the human subject at the second time point, of detectable autoantibodies directed against either or both of CTLD1 and CTLD7, or an increase in the second level of autoantibodies directed against either or both of CTLD1 and CTLD7 relative to the first level, indicates that the treatment being monitored is not effective; and
  administering to the human subject at least one additional treatment selected from the group consisting of immunosuppression, kidney dialysis and kidney transplant when the treatment being monitored is determined to be not effective.

2. The method of claim 1, wherein absence, from the second body fluid sample obtained from the human subject at the second time point, of detectable autoantibodies respectively directed against CysR, CTLD1 and CTLD7, or a decrease of the second levels of said autoantibodies relative to the respective first levels, indicates that the treatment being monitored is effective.

3. The method of claim 1, wherein said treatment is immunosuppressive therapy selected from the group consisting of cyclosporin, tacrolimus, azathioprine, infliximab, omalizumab, daclizumab, adalimumab, eculizumab, efalizumab, natalizumab, omalizumab and rapamycin, cyclophosphamide, chlorambucil, and rituximab.

4. The method of claim 1, wherein said treatment comprises symptomatic treatment that comprises renin-angiotensin system blockade.

5. A method for selecting and monitoring a treatment for a human subject suffering from membranous nephropathy or idiopathic membranous nephropathy, comprising:
- administering a treatment to be monitored, comprising renin-angiotensisn system blockade and/or diuretics, wherein administration of the monitored treatment may begin before, during or after obtaining a first body fluid sample;
- obtaining at a first time point the first body fluid sample selected from the group consisting of blood, serum and plasma;
- detecting in vitro a first level of at least one autoantibody selected from the group consisting of an autoantibody directed against C-type lectin domain 1 (CTLD1) of PLA2R1, and an autoantibody directed against C-type lectin domain 7 (CTLD7) of PLA2R1, in the first body fluid sample;
- obtaining at a second time point a second body fluid sample selected from the group consisting of blood, serum and plasma, wherein said first body fluid sample and said second body fluid sample are from a same body fluid;
- detecting in vitro a second level of said at least one autoantibody selected from the group consisting of an autoantibody directed against CTLD1 of PLA2R1, and an autoantibody directed against CTLD7 of PLA2R1 in the second body fluid sample, and
- comparing the first and second levels of the at least one autoantibody, wherein:
  - detecting an absence of the at least one autoantibody in the second body fluid sample directed against either or both of CTLD1 and CTLD7, or a decrease of the second level of the at least one autoantibody directed against either of CTLD1 and CTLD7 relative to the first level indicates that the monitored treatment is effective; and
- continuing administration of the monitored treatment without immunosuppression or hemodialysis; or
  - detecting a presence of the at least one autoantibody in the second body fluid sample directed against either or both of CTLD1 and CTLD7, or an increase in the second level of the at least one autoantibody directed against either or both of CTLD1 and CTLD7 relative to the first level indicates that the monitored treatment is not effective; and
- administering at least one additional treatment to the patient selected from the group consisting of immunosuppression, kidney dialysis and kidney transplant.

6. The method of claim 5, wherein the detecting steps are performed using an assay selected from the group consisting of agglutination test, enzyme-labeled immunoassay, ELISA, biotin/avidin assay, radioimmunoassay, immunoelectrophoresis, and immunoprecipitation.

7. The method of claim 5, wherein the detecting steps are performed by ELISA.

* * * * *